(12) United States Patent
Miyawaki et al.

(10) Patent No.: US 10,254,276 B2
(45) Date of Patent: Apr. 9, 2019

(54) ANTIBODY COMPOSITION, KIT FOR PREPARING ANTIBODY COMPOSITION, AND IMMUNOSTAINING METHOD

(71) Applicant: RIKEN, Saitama (JP)

(72) Inventors: Atsushi Miyawaki, Saitama (JP); Hiroshi Hama, Saitama (JP)

(73) Assignee: RIKEN, Saitama (JP)

( * ) Notice: Subject to any disclaimer, the term of this patent is extended or adjusted under 35 U.S.C. 154(b) by 770 days.

(21) Appl. No.: 14/410,784

(22) PCT Filed: Jul. 10, 2013

(86) PCT No.: PCT/JP2013/068889
§ 371 (c)(1),
(2) Date: Jun. 15, 2015

(87) PCT Pub. No.: WO2014/010633
PCT Pub. Date: Jan. 16, 2014

(65) Prior Publication Data
US 2015/0346196 A1  Dec. 3, 2015

(30) Foreign Application Priority Data

Jul. 10, 2012  (JP) ................. 2012-155060

(51) Int. Cl.
G01N 31/00 (2006.01)
G01N 33/53 (2006.01)
G01N 33/68 (2006.01)
C07K 16/18 (2006.01)

(52) U.S. Cl.
CPC ......... *G01N 33/5306* (2013.01); *C07K 16/18* (2013.01); *G01N 33/6854* (2013.01); *G01N 2333/47* (2013.01); *G01N 2800/28* (2013.01)

(58) Field of Classification Search
None
See application file for complete search history.

(56) References Cited

U.S. PATENT DOCUMENTS

2012/0128678 A1    5/2012    Aburatani

FOREIGN PATENT DOCUMENTS

| JP | 4-329357 | 11/1992 |
|---|---|---|
| JP | 2006-194746 | 7/2006 |
| JP | 2011-16763 | 1/2011 |

OTHER PUBLICATIONS

Claudio Montero (The Journal of Histochemistry & Cytochemistry, vol. 51, pp. 1-4, 2003).*
Hayashi et al. (Histochem Cell Biol. Jun. 2011, 135(6), 627-637).*
International Search Report, International Patent Application No. PCT/JP2013/068889, dated Aug. 6, 2013.
International Preliminary Report on Patentability, International Patent Application No. PCT/JP2013/068889, dated Jan. 22, 2015, English translation provided.
Lakoma et al., "Reelin sets the pace of neocortical neurogenesis." Development, 2011, 138, 5223-5234.
Miyawaki A., "Honyurui Dobutsu no KoteiSoshiki no Diakibo—Koseisai 3 Jigen Keiko Kansatsu." DOjin news, 2012, No. 143, pp. 6-9.
Shan-Rong-Shi, "Use of pH 9.5 Tris-HCI Buffer Containing 5% Urea for Antigen Retrieval Immunohistochemistry." Biotechnic & Histochemistry, 1996, vol. 71/No. 4, pp. 190-196.

* cited by examiner

*Primary Examiner* — Lisa V Cook
(74) *Attorney, Agent, or Firm* — Casimir Jones, SC; Robert A. Goetz

(57) ABSTRACT

An antibody composition, which is an aspect of the present invention, contains at least one compound selected from the group consisting of urea and urea derivatives, the compound being contained in the antibody composition at a concentration of not less than 0.1 M and less than 1 M, the antibody composition being a solution.

8 Claims, 7 Drawing Sheets

ANTIBODY COMPOSITION, KIT FOR PREPARING ANTIBODY COMPOSITION, AND IMMUNOSTAINING METHOD

CROSS REFERENCE TO RELATED APPLICATIONS

The present application is a Section 371 U.S. national stage entry of pending International Patent Application No. PCT/JP2013/068889, International Filing Date Jul. 10, 2013, which claims the benefit of Japanese Patent Application No. 2012-155060, filed Jul. 10, 2012, the contents of which are incorporated by reference in their entireties.

TECHNICAL FIELD

The present invention relates to an antibody composition, a kit for preparation of an antibody composition, and an immunostaining method.

BACKGROUND ART

Antibodies, by virtue of their abilities of specifically binding to targets (antigens) in the antigen-antibody reactions, are used in many fields including pharmaceuticals, diagnostic agents, and reagents. Antibodies as reagents, in particular, are used in many experimental methods extending from quantitative analysis methods (including semi-quantitative analysis) such as a Western blotting method and an ELISA method to qualitative and semi-quantitative analysis methods such as immunohistostaining. Possible strategies for making effective use of antibodies include enhancing the reactivity of antibodies or reducing background noise caused by non-specific adsorption of antibodies.

A commonly used method for reducing background noise caused by non-specific adsorption of antibodies is, for example, a blocking method using a blocking reagent such as skimmed milk (Non-Patent Literature 1).

Meanwhile, due to the development of microscopic techniques in recent years, attention has been focused on observation of a deep portion of a subject in histological analysis.

CITATION LIST

Non-Patent Literature

Non-Patent Literature 1
Lakoma et al. Development 138:5223-5234, 2011.

SUMMARY OF INVENTION

Technical Problem

In immunohistochemical analysis, a subject to be observed, even its section, inevitably has a thickness. In a case where the subject to be observed has a large thickness, enhancement in infiltrating property of antibodies enables biological staining of a deep portion of a subject, thus being useful for analysis of three-dimensional structure.

The present invention has been attained to solve the above problem, and an object thereof is to provide an antibody composition including (i) a predetermined compound enhancing infiltrating property of an antibody with respect to a biological material such as a tissue and (ii) an antibody, use of the antibody composition, and others.

Solution to Problem

In order to solve the above problem, the present invention provides any of the followings:

(1) An antibody composition including:
at least one compound selected from the group consisting of urea and urea derivatives; and
an antibody,
the compound being contained in the antibody composition at a concentration of not less than 0.1 M and less than 1 M,
the antibody composition being a solution.

(2) A kit for preparation of an antibody composition, including:
a solution containing at least one compound selected from the group consisting of urea and urea derivatives; and
an instruction manual for the kit,
the instruction manual including the following instructions:
1) mix the solution and an antibody to prepare an antibody composition; and
2) prepare the antibody composition such that a final concentration of the compound in the antibody composition is not less than 0.1 M and less than 1 M.

(3) An immunostaining method including:
a step of bringing (i) an antibody composition as set forth in (1) in which the antibody is an antibody for immunostaining and (ii) a biological material into contact with each other.

Advantageous Effects of Invention

The present invention can provide a novel antibody composition including (i) a predetermined compound that enhances infiltrating property of an antibody with respect to a biological material such as a tissue and (ii) an antibody, use of the antibody composition, and others.

DESCRIPTION OF EMBODIMENTS

Figure 1:
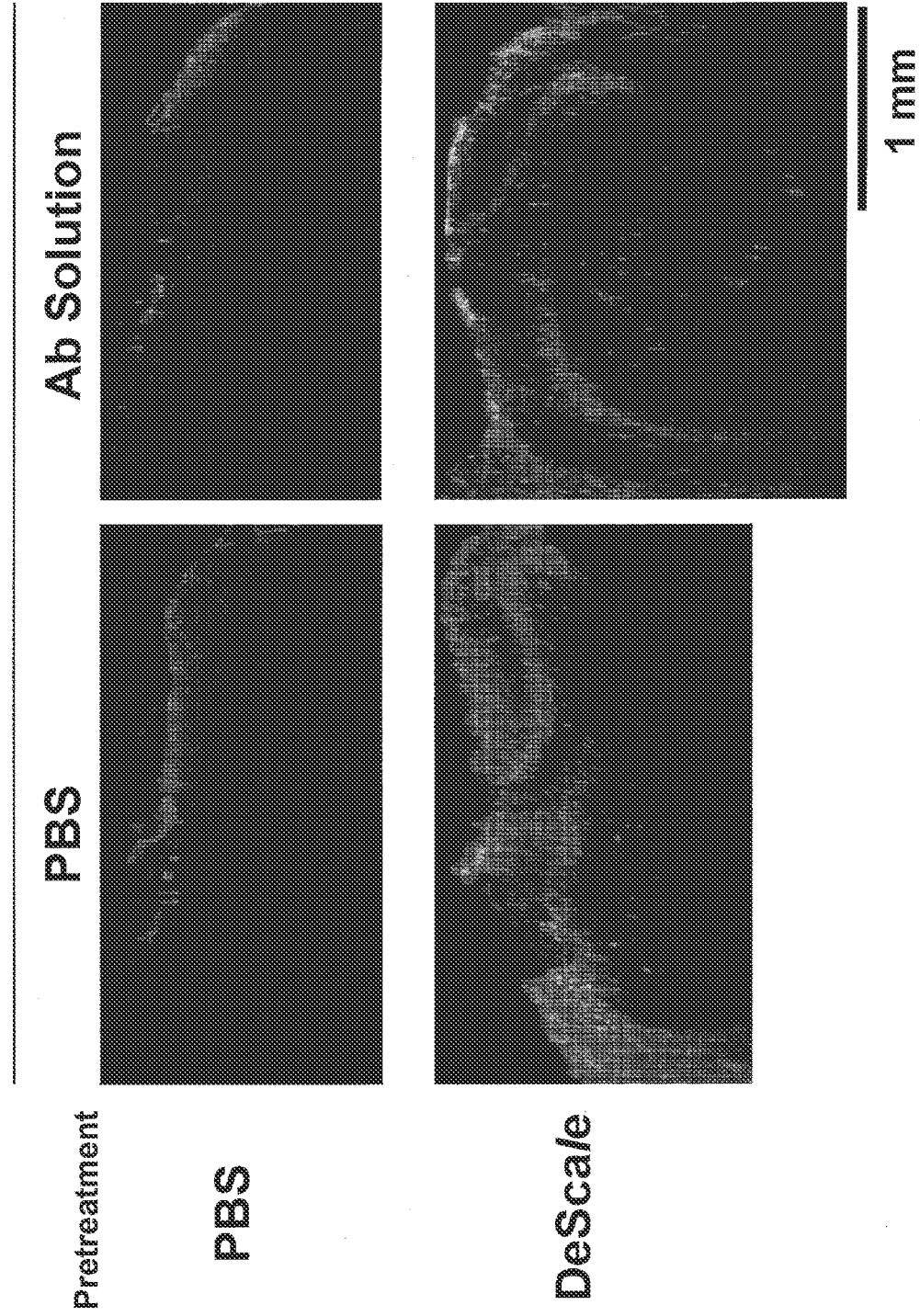
FIG. 1 is a view showing the result of an example according to the present invention.

The following will describe an embodiment of the present invention in detail.

[1. Antibody Composition]

An antibody composition according to the present invention contains (i) at least one compound selected from the group consisting of urea and urea derivatives and (ii) an antibody, the compound being contained in the antibody composition at a concentration of not less than 0.1 M and less than 1 M, the antibody composition being a solution.

(Urea Derivative)

Concretely, the urea derivative is, for example, any of various kinds of ureine or compounds expressed by Formula (1) below. Note that the compounds expressed by Formula (1) include part of ureines. The antibody composition according to the present invention only needs to contain at least one compound selected from the group consisting of urea and urea derivatives. Among these, the antibody composition more preferably contains urea.

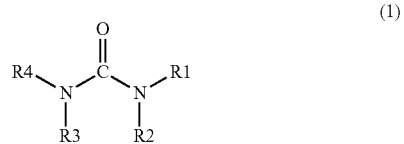

(1)

In a urea derivative expressed by Formula (1), each of R1, R2, R3, and R4 is independently a hydrogen atom (note that the one in which all of R1 through R4 are hydrogen atoms is excluded, since it corresponds to urea), a halogen atom, or a hydrocarbon group. Further, in a case where the hydrocarbon group has a plurality of carbon atoms, part of the carbon atoms may be replaced by a hetero atom such as a nitrogen atom, an oxygen atom, or a sulfur atom. Examples of the hydrocarbon group encompass a chain hydrocarbon group and a cyclic hydrocarbon group.

Examples of the chain hydrocarbon group encompass a chain alkyl group, a chain alkenyl group, and a chain alkynyl group. The chain hydrocarbon group may have any number of carbon atoms. For example, the chain hydrocarbon group may be straight-chain or branched one having 6 or less carbon atoms, preferably, an alkyl group having 1 through 3 carbon atoms. The chain hydrocarbon group may have a substituent such as a halogen atom. Examples of the chain alkyl group encompass a methyl group, an ethyl group, a propyl group, an isopropyl group, a butyl group, an iso-butyl group, a sec-butyl group, a tert-butyl group, a hexyl group, and an octyl group.

The cyclic hydrocarbon group may be, for example, a cycloalkyl group or a cycloalkenyl group. The cyclic hydrocarbon group may have a substituent such as a halogen atom. Examples of the cycloalkyl group encompass those having 3 or more and preferably not more than 6 carbon atoms, such as a cyclopropyl group, a cyclobutyl group, a cyclopenthyl group, and a cyclohexyl group. Examples of the cycloalkenyl group encompass those having 3 or more and preferably not more than 6 carbon atoms, such as a cyclohexenyl group.

Examples of the halogen atom encompass a fluorine atom, a chlorine atom, a bromine atom, and an iodine atom.

The following 1) and 2) are more preferable, concrete examples of the urea derivatives expressed by Formula 1:

1) Any three groups selected from R1 through R4 are hydrogen atoms, and the other one group is (i) a halogen atom or (ii) a chain hydrocarbon group having 1 through 6 carbon atoms, more preferably, the other one group is an alkyl group having (i) 1 through 3 carbon atoms or (ii) 1 or 2 carbon atoms.

2) Any two groups selected from R1 through R4 are hydrogen atoms, and each of the other two groups is independently (i) a halogen atom or (ii) a chain hydrocarbon group having 1 through 6 carbon atoms, more preferably, both of the other two groups are alkyl groups each having (i) 1 through 3 carbon atoms or (ii) 1 or 2 carbon atoms. Still more preferably, one of the two groups which are hydrogen atoms is selected from R1 and R2, and the other of the two groups is selected from R3 and R4.

(Concentration of the Compound in the Antibody Composition)

In the antibody composition, at least one compound selected from the group consisting of urea and urea derivatives is contained at a concentration in a range from not less than 0.1 M to less than 1 M. An antibody composition containing the compound at a concentration of not less than 1 M is unfavorable since it may decrease the reactivity of the antibody to the antigen. In the case where the compound contained in the antibody composition is two or more kinds of compounds, the concentration in the range from not less than 0.1 M to less than 1M refers to a total concentration of these compounds.

The concentration of the compound in the antibody composition is preferably not less than 0.2 M and not more than 0.5 M, more preferably not less than 0.25 M and not more than 0.45 M, still more preferably not less than 0.27 M and not more than 0.4 M, and particularly preferably not less than 0.3 M and not more than 0.36 M.

(Antibody)

The antibody in the antibody composition is not limited to any specific kind. The antibody is, for example, an antibody for immunostaining. Alternatively, the antibody is an immunoglobulin derived from (a) a hybridoma culture supernatant, (b) ascites, anti-serum, or plasma of an intrasplenically immunized animal, or (c) a serous fluid of an egg of a bird. Use of an antibody composition according to the present invention is applicable to any uses that require maintaining antigen-antibody reactivity while enhancing infiltrating property with respect to subject biological materials such as tissues. Specifically, the antibody composition according to the present invention is used for, for example, immunostaining. Particularly preferably, the antibody composition according to the present invention is used for immunostaining containing a primary antibody for immunostaining and, if necessary, a secondary or higher order antibody for immunostaining.

(Concentration of the Antibody in the Antibody Composition)

The concentration of the antibody in the antibody composition is not particularly limited, but is preferably not less than 0.05 µg/mL and not more than 100 µg/mL, and more preferably not less than 4 µg/mL and not more than 40 µg/mL, from the viewpoint of increasing infiltrating property of the antibody to a biological material such as a tissue.

(Surfactant)

An "antibody composition" according to the present invention may contain a surfactant, if necessary. The surfactant is preferably a nonionic surfactant. Examples of the nonionic surfactant encompass: fatty acid surfactants such as polyoxyethylene sorbitan monolaurate, polyoxyethylene sorbitan monopalmitate, polyoxyethylene sorbitan monostearate, and polyoxyethylene sorbitan monooleate; higher alcohol surfactants such as polyvinyl alcohol; and alkylphenol surfactants such as polyoxyethylene octylphenyl ether. Specifically, for example, the surfactant may be at least one selected from the group consisting of: TRITON X (Registered Trademark) series such as TRITON X-100 and TRITON X-140; TWEEN (Registered Trademark) series such as TWEEN-20, TWEEN-40, TWEEN-60, and TWEEN 80; and NP-40 (product name). As the surfactant, a mixture of two or more kinds may be used, if necessary.

The concentration of the surfactant in the antibody composition is not particularly limited, but is preferably not less than 0.025 (w/v) % and not more than 0.2 (w/v) %, and more preferably not less than 0.05 (w/v) % and not more than 0.1 (w/v) %, from the viewpoint of increasing permeability of the antibody composition to a subject biological material. Note that the unit "(w/v) %" represents a percentage of a weight (w (gram)) of a surfactant used, with respect to a volume (v (milliliter)) of the "antibody composition." The same meaning of this unit also applies to components other than the surfactant.

(Other Components)

The "antibody composition" according to the present invention can contain a component selected from, for example, sugars and alcohols, if necessary. Examples of the sugars encompass: sucrose, fructose, sorbitol, trehalose, and cyclodextrin. Sucrose is contained at a concentration of, for example, not less than 1 (w/v) % and not more than 5 (w/v) %. Fructose, sorbitol, and trehalose are each contained at a concentration of, for example, not less than 50 mg/mL and not more than 200 mg/mL. Cyclodextrin is contained at a concentration of, for example, not less than 50 mg/mL and not more than 150 mg/mL. An alcohol, which is exemplified by glycerol, is contained at a concentration of, for example, not less than 1 (w/v) % and not more than 5 (w/v) %.

(Solvent)

An "antibody composition" according to the present invention is a solution containing a solvent in which urea or a urea derivative is soluble. The solvent is not limited to any specific kind, as long as urea or a urea derivative is soluble in the solvent. Preferably, water is used as a main solvent; particularly preferably, only water is used as the solvent. Note that, in the present invention, what is meant by the expression "water is used as a main solvent" is that a volumetric percentage of water to all solvents used is larger than that of any other solvent, and preferably that water is used in an amount which accounts for more than 50% and not more than 100% of a total volume of all solvents used. An "antibody composition" prepared by using water as a main solvent can be referred to as an "antibody composition" in the form of an aqueous solution.

An "antibody composition" according to the present invention may be a buffer containing an antibody and at least one compound selected from the group consisting of urea and urea derivatives. Examples of the buffer encompass an equilibrium salt solution (e.g., PBS and HBSS) which is buffered by phosphate and an equilibrium salt solution (TBS) which is buffered by tris hydrochloride. A concentration (synonymous with dilution degree) of the buffer is not particularly limited, but is preferably not lower than 0.05 fold and not higher than 1.5 fold, more preferably not lower than 0.1 fold and not higher than 1 fold. The buffer can be interpreted as one kind of the above aqueous solution.

(Preparation of the Antibody Composition)

An "antibody composition" according to the present invention is prepared by adding, to a solvent, "urea and/or a urea derivative (compound)", "antibody," and "surfactant", etc. used as needed. The procedure of adding the constituent components of the antibody composition is not limited to any particular one. In one example, an antibody solution is mixed with "urea and/or a urea derivative (compound)" and a component(s) used as needed, such as "surfactant," "sugar," and "alcohol", at intended final concentrations as described above.

(Role, Etc. Of the Compound in the Antibody Composition)

An antibody composition containing at least one compound selected from the group consisting of urea and urea derivatives at a concentration of not less than 0.1 M and less than 1 M increases infiltrating property of the antibody to a biological material such as a tissue. That is, the present invention can also be interpreted as any one of the followings 1) and 2):

1) A method of treating an antibody with a solution containing at least one compound selected from the group consisting of urea and urea derivatives at a concentration of not less than 0.1 M and less than 1 M, thus increasing infiltrating property of the antibody to a biological material such as a tissue; and 2) A use of a solution containing at least one compound selected from the group consisting of urea and urea derivatives at a concentration of not less than 0.1 M and less than 1 M, wherein treating an antibody with the solution increases infiltrating property of the antibody to a biological material such as a tissue. Note that the solution may further contain the above-described component(s) such as a surfactant. Further, in both of the above cases 1) and 2), the concentration of the compound is preferably not less than 0.2 M and not more than 0.5 M, more preferably not less than 0.25 M and not more than 0.45 M, still more preferably not less than 0.27 M and not more than 0.4 M, and particularly preferably not less than 0.3 M and not more than 0.36 M.

[2. Kit for Preparation of an Antibody Composition]

A kit for preparation of an antibody composition according to the present invention includes: a solution containing at least one compound selected from the group consisting of urea and urea derivatives; and an instruction manual for the kit, and the instruction manual includes the following instructions:

1) mix the solution and an antibody to prepare an antibody composition; and 2) prepare the antibody composition such that a final concentration of the compound in the antibody composition is not less than 0.1 M and less than 1 M.

Note that the solvent, antibody, and urea derivative, which constitute the solution, refer to the same ones as described above in Section [1. Antibody composition]. The solution is contained in, for example, a lid-equipped solution container or a solution stowage bag.

Further, the instruction manual for the kit is a record of the antibody composition preparation method as described above in Section (Preparation of the antibody composition). The instruction manual may be printed on, for example, a recording medium such as a sheet of paper or may be electronically recorded in an electronic recording medium such as a floppy Disk®, a compact disc (CD), a MD, or flash memory.

In one aspect, the solution contains a surfactant in such a manner that a final concentration of the surfactant contained in the antibody composition is not less than 0.025 (w/v) % and not more than 0.2 (w/v) % and more preferably not less than 0.05 (w/v) % and not more than 0.1 (w/v) %. Note that the surfactant refers to the same one as described above in Section [1. Antibody composition].

If necessary, the solution can further contain other component(s), such as a sugar and an alcohol, as described above in Section [1. Antibody composition].

As to the components contained in the solution, their concentrations are substantially maintained as they are or diluted in the preparation of an antibody composition by mixing the antibody with the solution. If initial concentrations of the components contained in the solution are specified in the kit, it is possible to use the kit in such a manner that the final concentrations of the components in the antibody composition are adjusted to the predetermined values as described above.

In a case where the solution contains a plurality of components including at least one compound selected from the group consisting of urea and urea derivatives, a surfactant, a sugar, and an alcohol, the solution only needs to contain these components in a ratio that is identical to a ratio of final concentrations of these components in the antibody composition. Examples of the solution containing a plurality of components encompass the following solution:

<Solution 1>

Concentration of urea or a urea derivative is not less than 0.1 M and less than 1M, Concentration of a surfactant is not less than 0.05 (w/v) %, and not more than 0.1 (w/v) %, and A solvent is PBS.

A kit for preparation of an antibody composition according to the present invention may further contain an antibody solution, which is different from the above solution. The antibody solution is contained in, for example, a lid-equipped antibody solution container or an antibody solution stowage bag. As described above in Section (Preparation of the antibody composition), the antibody solution is the one for being mixed with the above solution to prepare an antibody composition. The kit for preparation of an antibody composition may include two or more kinds of antibody solutions. When an antibody for immunostaining is taken as an example, the kit for preparation of an antibody composition includes, for example, an antibody solution containing a primary antibody and an antibody solution containing a secondary or higher order antibody. Further, in a case where the kit for preparation of an antibody composition includes the antibody solution(s), the kit may further include, for example, a mixture container for use in mixture of the antibody solution(s) with the above solution.

[3. Immunostaining Method Using an Antibody Composition]

An example of use of an antibody composition according to the present invention is immunostaining. For use in immunostaining, the antibody composition contains a primary antibody for immunostaining or a secondary or higher order antibody used as needed. The immunostaining method includes a step of bringing the antibody composition according to the present invention and a biological material into contact with each other.

(Biological Material to be Subjected to Immunostaining)

A biological material to be subjected to immunostaining using an antibody composition according to the present invention is not limited to any specific kind. Preferably, the biological material is a material derived from a plant or an animal, more preferably a material derived from an animal such as the one selected from fish, amphibians, reptiles, birds, and mammals, particularly preferably a material derived from a mammal. The mammal is not limited to any specific kind, examples of which encompass: laboratory animals such as mice, rats, rabbits, guinea pigs, and primates except for humans; pet animals such as dogs and cats; farm animals such as cows and horses; and humans.

Alternatively, the biological material may be an individual itself (except for a living human individual). Further alternatively, the biological material may be a part of a biological organism such as an organ, a tissue, or a cell of a multicellular organism. The part of a biological organism such as an organ, a tissue, or a cell of a multicellular organism may be taken from an individual or may be artificially prepared in vitro. The biological material is preferably an individual itself of a biological organism, an organ taken from an individual of a biological organism, or a tissue taken from an individual of a biological organism. The individual, organ, and tissue of a biological organism may be subjected to immunostaining with their own shapes unchanged or may be subjected to immunostaining in the form of slices. Moreover, the biological material may be the one in which, for example, a fluorescent protein(s) is expressed.

Note that a method for preparation of a biological specimen by using the above biological material as a sample for immunostaining can be a general method for preparation of a slice sample for immunostaining or a method for preparation of a whole mount sample. As an example, in preparation of a slice sample for immunostaining, a biological material is fixed if necessary, and then embedded into, for example, paraffin, after which the biological material is cut into slices or processed into frozen slices or the like. Depending on the type of slice sample, a clearing treatment may be performed if necessary. In another example, in preparing a whole mount sample for immunostaining, a fixing treatment and a clearing treatment are performed if necessary.

(Example of Immunostaining Method and Observation Method)

The following describes an example of a schematic flow of immunostaining using an antibody composition according to the present invention and an observation method. Note that all of the steps described below may be carried out under the same conditions as in a widely known immunostaining method.

Step 1: A step of preparing the above sample for immunostaining.

Step 2: A step of subjecting the sample having been prepared in the Step 1 to an antigen activation treatment (the Step 2 is performed if the need arises). This step is realized by performing, for example, a heat treatment or a proteolytic treatment.

Step 3: A step of performing a treatment for reducing background noise (the Step 3 is performed if the need arises). This step is realized by performing, for example, a RNA degradation treatment for preventing contamination of unwanted RNA or a blocking treatment with a blocking reagent such as serum or skimmed milk.

Step 4: An antigen-antibody reaction treatment step of performing a treatment for an antigen-antibody reaction of the sample for immunostaining, which sample has undergone the Steps 1 to 3, and an antibody composition containing a primary antibody for immunostaining. The conditions of incubation in the antigen-antibody reaction treatment step may be determined depending on performance of the antibody, a size of the sample, and others. For example, the incubation is performed by shaking for a time period ranging from six hours to five days and preferably two to three days. Further, the incubation is preferably performed at a temperature of, for example, about 4° C. A specific example of a concentration of the primary antibody in the antibody composition includes a concentration of not less than 4 μg/mL and not more than 40 μg/mL.

Step 5: A cleaning step of cleaning the sample for immunostaining, which sample has undergone the Step 4. The cleaning step is, for example, rinsing of the sample with a solution containing at least one compound selected from the group consisting of urea and urea derivatives at a concentration of not less than 0.1 M and less than 1 M. The use amount of the solution is not limited to any specific amount, but is, for example, 9 to 15 ml for each 0.3 g of sample and preferably approximately 12 ml for each 0.3 g of sample. A temperature of the cleaning step and a length of time for the cleaning step are not particularly limited. Preferably, the sample is rinsed by shaking at room temperature for about one hour.

Step 6: An antigen-antibody reaction treatment step of performing a treatment for an antigen-antibody reaction of the sample for immunostaining, which sample has undergone the Step 5, and an antibody composition containing a secondary or higher order antibody for immunostaining. The conditions of incubation in the antigen-antibody reaction treatment step may be determined depending on performance of the antibody, a size of the sample, and others. For example, the incubation is performed by shaking for a time period ranging from six hours to five days and preferably two to three days. Further, the incubation is preferably performed at a temperature of, for example, about 4° C. A specific example of a concentration of the secondary or higher order antibody in the antibody composition includes a concentration of not less than 1 μg/mL and not more than 10 μg/mL.

Step 7: A step of cleaning the sample for immunostaining, which sample has undergone the Step 6. More specifically, the Step 7 is performed in the same manner as in the Step 5.

Step 8: A step of visualizing an antigen-antibody reaction of the sample for immunostaining, which sample has undergone the Steps 1 through 7 (the Step 8 is performed if the need arises). For example, in a case where the primary antibody or the secondary or higher order antibody is labeled with an enzyme such as alkaline phosphatase, the sample is allowed to react in a substrate of the enzyme, with the result that pigmentation of the sample with a dye generated by the reaction occurs for visualization. In a case where the primary antibody or the secondary or higher order antibody is labeled with a fluorescent dye such as fluorescein or rhodamine, the sample is observed in Step 9, which is described later, through a fluorescence microscope while being visualized directly by the fluorescence microscope.

Step 9: An observation step of observing the immunostained sample for immunostaining, which sample has undergone the Steps 1 to 8, through an optical microscope. The observation step can be performed with use of any type of optical microscope. In a case where the sample for immunostaining is to be observed three-dimensionally, the observation step can be performed by employing, for example, a three-dimensional super-resolution microscopy technique (e.g., STED, 3D PALM, FPALM, 3D STORM, or SIM). Preferably, the observation step is performed by employing a multi-photon excitation type (generally, two-photon excitation type) optical microscopy technique.

In the above schematic flow, if the Step 4 is performed and the Step 6 is skipped, the antibody composition used in the Step 4 is the antibody composition according to the present invention. In a case where both the Steps 4 and 6 are performed, at least one of the antibody compositions used in the Steps 4 and 6 is the antibody composition according to the present invention. Preferably, both of the antibody compositions used in the Steps 4 and 6 are the antibody composition according to the present invention.

Note that, in the above schematic flow, the sample for immunostaining may be subjected to a clearing treatment in the Step 1 or prior to the Step 1. The clearing treatment is, for example, the one as described in PCT international publication No. WO 2011/111876 A1 (U.S. patent application Ser. No. 13/583,548) in which a clearing treatment is performed on a sample with a clearing reagent for a biological material, the reagent containing, as an active component, at least one compound selected from the group consisting of urea and urea derivatives. The disclosure of PCT international publication No. WO 2011/111876 A1 (U.S. patent application Ser. No. 13/583,548) are incorporated herein by reference in its entirety. The compound is identical to a compound constituting the antibody composition according to the present invention. However, the concentration of the compound used in the clearing treatment is preferably not less than 1 M and not more than 8.5 M, more preferably not less than 3 M and not more than 5 M, further preferably not less than 3.5 M and not more than 4.5 M, and particularly preferably not less than 3.7 M and not more than 4.3 M. A processing time for which the clearing treatment is performed is not particularly limited, but is, for example, within a range of not less than two hours and not more than one year, preferably within a range of not less than two hours and not more than six months, more preferably within a range of not less than 72 hours and not more than 21 days.

A clearing treatment using the "clearing reagent for making a biological material transparent" is reversible. As such, a biological material having been subjected to the clearing treatment can be brought back to a state that it had before the clearing treatment, e.g., by immersing the biological material in an equilibrium salt solution so as to remove therefrom the components of the clearing reagent. Here, specific examples of the equilibrium salt solution encompass: equilibrium salt solutions (e.g., PBS and HBSS) which are buffered by phosphate; an equilibrium salt solution (TBS) which is buffered by tris hydrochloride; an artificial cerebrospinal fluid (ACSF); and basal media for cell culturing, such as MEM, DMEM, and Ham's F-12. A time for which the biological material is immersed in the equilibrium salt solution is not particularly limited, but is, for example, two hours to 24 hours. The immersion treatment is performed at a temperature, for example, in a range from approximately 4° C. to room temperature and preferably at approximately 4° C. or room temperature.

By performing immunostaining with use of an antibody composition according to the present invention on a sample having been subjected to the clearing treatment with use of the above clearing reagent for a biological material, it is possible to realize immunostaining having a higher sensitivity. Note that even in a case where a sample having been subjected to the clearing treatment is brought back to a state that the sample had before the clearing treatment and is then subjected to immunostaining, a similar effect is yielded.

(Exemplification of Specific Aspect of the Present Invention)

A specific aspect of the present invention is any of the aspects described below. A specific aspect of the present invention enhances infiltrating property of an antibody with respect to a biomaterial and is thus useful for analysis of three-dimensional structure of a subject in, for example, analysis of immunohistostaining. This makes it possible to three-dimensionally analyze a pathological tissue, which was two-dimensionally analyzed in the past. This can serve a useful function in understanding a pathologic condition of a disease and raise the possibility of new drug development.

(1) An antibody composition including:
  at least one compound selected from the group consisting of urea and urea derivatives; and
  an antibody,
  the compound being contained in the antibody composition at a concentration of not less than 0.1 M and less than 1 M,
  the antibody composition being a solution.

(2) The antibody composition as set forth in (1), wherein the compound is contained at a concentration of not less than 0.2 M and not more than 0.5 M.

(3) The antibody composition as set forth in (1) or (2), further including:
a surfactant.

(4) The antibody composition as set forth in (3), wherein the surfactant is a nonionic surfactant.

(5) The antibody composition as set forth in (4), wherein the nonionic surfactant is at least one selected from the group consisting of TRITON X (Registered Trademark), TWEEN (Registered Trademark), and NP-40 (product name).

(6) The antibody composition as set forth in any one of (3) through (5), wherein
the surfactant is contained at a concentration of not less than 0.025 (w/v) % and not more than 0.2 (w/v) %.

(7) The antibody composition as set forth in any one of (1) through (6), wherein
the antibody is contained at a concentration of not less than 0.05 μg/mL and not more than 100 μg/mL.

(8) The antibody composition as set forth in any one of (1) through (7), wherein
urea is contained as the compound.

(9) The antibody composition as set forth in any one of (1) through (8), wherein
the antibody is an antibody for immunostaining.

(10) A kit for preparation of an antibody composition, including:
a solution containing at least one compound selected from the group consisting of urea and urea derivatives; and
an instruction manual for the kit,
the instruction manual including the following instructions:
1) mix the solution and an antibody to prepare an antibody composition; and
2) prepare the antibody composition such that a final concentration of the compound in the antibody composition is not less than 0.1 M and less than 1 M.

(11) The kit as set forth in (10), wherein
the solution contains a surfactant so that a final concentration of the surfactant in the antibody composition is not less than 0.025 (w/v) % and not more than 0.2 (w/v) %.

(12) The kit as set forth in (10) or (11), wherein
the solution is a buffer.

(13) The kit as set forth in any one of (10) through (12), further including:
an antibody solution.

(14) An immunostaining method including:
a step of bringing an antibody composition as set forth in (9) and a biological material into contact with each other.

EXAMPLES

The following will further specifically describe the present invention with reference to Examples, Comparative Examples, etc. below. However, the present invention is not limited to these.

Example 1: Antibody Permeability Promoting Effect of the Antibody Composition According to the Present Invention In the present Example, staining of an entire hippocampus of a 3 week-old ICR mouse (purchased from Japan SLC, Inc.) was carried out with use of NeuN-Cy5 and GFAP-Cy3 in a manner described below. Specifically, at the stage of sample preparation performed before the staining, a right hippocampus of a mouse brain was immersed in a solution A and was then shaken for seven days at room temperature. Thereafter, the right hippocampus was subjected to immersion treatment in a 1×PBS for twelve hours. A left hippocampus derived from the same brain was immersed for 7.5 days in a 1×PBS and shaken at 4° C. in order to prevent deterioration of a tissue thereof. Note that the solution A is an aqueous solution prepared by dissolving 4M urea, 0.1% (w/v) TRITON X-100 (Registered Trademark), and 10% (w/v) glycerol in pure water.

Subsequently, antibody compositions were obtained by diluting individual antibodies with 1 ml of 1×PBS, and another antibody compositions were obtained by diluting individual antibodies with 1 ml of antibody treatment solution (Ab-solution). Then, varying combinations of these antibody compositions and the hippocampi prepared by the above-described treatment were each shaken at 4° C. for four days, thereby being reacted with each other for staining. Note that the antibodies used in the present Example are (i) a Cy3 dye-labeled anti-GFAP mouse monoclonal antibody (Sigma, Clone G-A-5; referred to as GFAP-Cy3) whose antigen is GFAP serving as a marker of an astrocyte and (ii) an anti-NeuN mouse monoclonal antibody (Millipore; referred to as NeuN-Cy5) which was self-labeled with a Cy5 reactive dye (GE Healthcare). As for the anti-NeuN mouse monoclonal antibody, its antigen is a transcription factor specific to a neuron. Note that each of the above antibody compositions was composed of an antibody solution containing any one of the antibodies (i) and (ii) and a treatment solution (PBS or an antibody treatment solution) both of which were mixed in a volume ratio of 1:300, and an antibody concentration thereof was as follows: GFAP-Cy3 concentration is 7 μg/mL, and NeuN-Cy5 concentration is 3 μg/mL. Further, the antibody treatment solution is an aqueous solution composed of 0.33M urea, 0.1% (w/v) TRITON X-100 (Registered Trademark), and 1×PBS.

After the staining, treatments were carried out in accordance with an operation flow as described below. Specifically, the hippocampi were rinsed with the individual solutions used for dilution of the antibodies and were then refixed, after which the hippocampi were treated in the solution A at room temperature for two days. Then, the hippocampi thus treated were mounted with use of 0.35 (w/v) % agarose. Subsequently, the hippocampi (7 μm-thick optical sections) were subjected to multipoint continuous observation, from the surfaces thereof to the deep portions thereof, through a laser scanning-type confocal upright microscope FV1000 (Olympus) equipped with a 20-power water immersion objective lens (Olympus; W.D.: 2 mm, NA: 0.95), after which image analysis was carried out by analysis software named Volocity (Perkin Elmer). Note that the observation was performed in the solution A.

<Operation Flow after the Staining>

First, after incubation for the staining, the hippocampi were rinsed by shaking with a PBS (12 ml for each 0.3 g of hippocampal tissue) or with the above-described antibody treatment solution at room temperature for one hour. Secondly, the hippocampi were rinsed by shaking with a mixture solution (12 ml for each 0.3 g of hippocampal tissue) of 2.5 (w/v) % bovine serum albumin (BSA), 0.05 (w/v) % Tween 20, and 0.1×PBS at room temperature for one hour. Finally, the hippocampi were refixed, by shaking, in a 4% PFA-PBS (12 ml for each 0.3 g of hippocampal tissue) at room temperature for one hour.

The results are shown in FIG. 1. The antibodies reached deeper portions of both of the hippocampi (lower ones in FIG. 1) subjected to the immersion treatment in the solution A at the stage of sample preparation, as compared with the hippocampi (upper ones in FIG. 1) subjected to the immersion treatment in the PBS, and significant antigen recognition thereof was observed. Particularly, for the antibodies diluted with the antibody treatment solution and allowed to react, it was observed that the antibodies permeated into and reached a further deeper portion (a depth of approximately 2 mm from the surface), as compared with the antibodies diluted with the PBS and allowed to react (a depth of approximately 1.5 mm from the surface).

Example 2: Staining Properties of the Anti-GFAP Monoclonal Antibody with Respect to Cerebrum of YFP-H Line Mouse An entire cerebrum of a 8 week-old YFP-H line mouse (provided by Professor Josh Sanes of Harvard University, U.S.A. [reference] Feng et al. Neuron, 28: 41-51, 2000) was subjected to immersion treatment in the solution A for one month and then subjected to immersion treatment in a 1×PBS for three hours. Thereafter, the cerebrum was stained with an antibody composition which was prepared by diluting a Cy3 dye-labeled anti-glial fibrillary acidic protein (GFAP) mouse monoclonal antibody (Sigma, Clone G-A-5) with 1 ml of antibody treatment solution (identical to the one used in Example 1). As in Example 1, the antibody composition was composed of an antibody solution containing the antibody and the antibody treatment solution both of which were mixed in a volume ratio of 1:300, and an antibody concentration thereof was 7 µg/mL. The staining was carried out in such a manner that the antibody composition and the mouse cerebrum prepared by the above-described treatment were shaken at 4° C. for five days while coexisting with each other.

Figure 2:
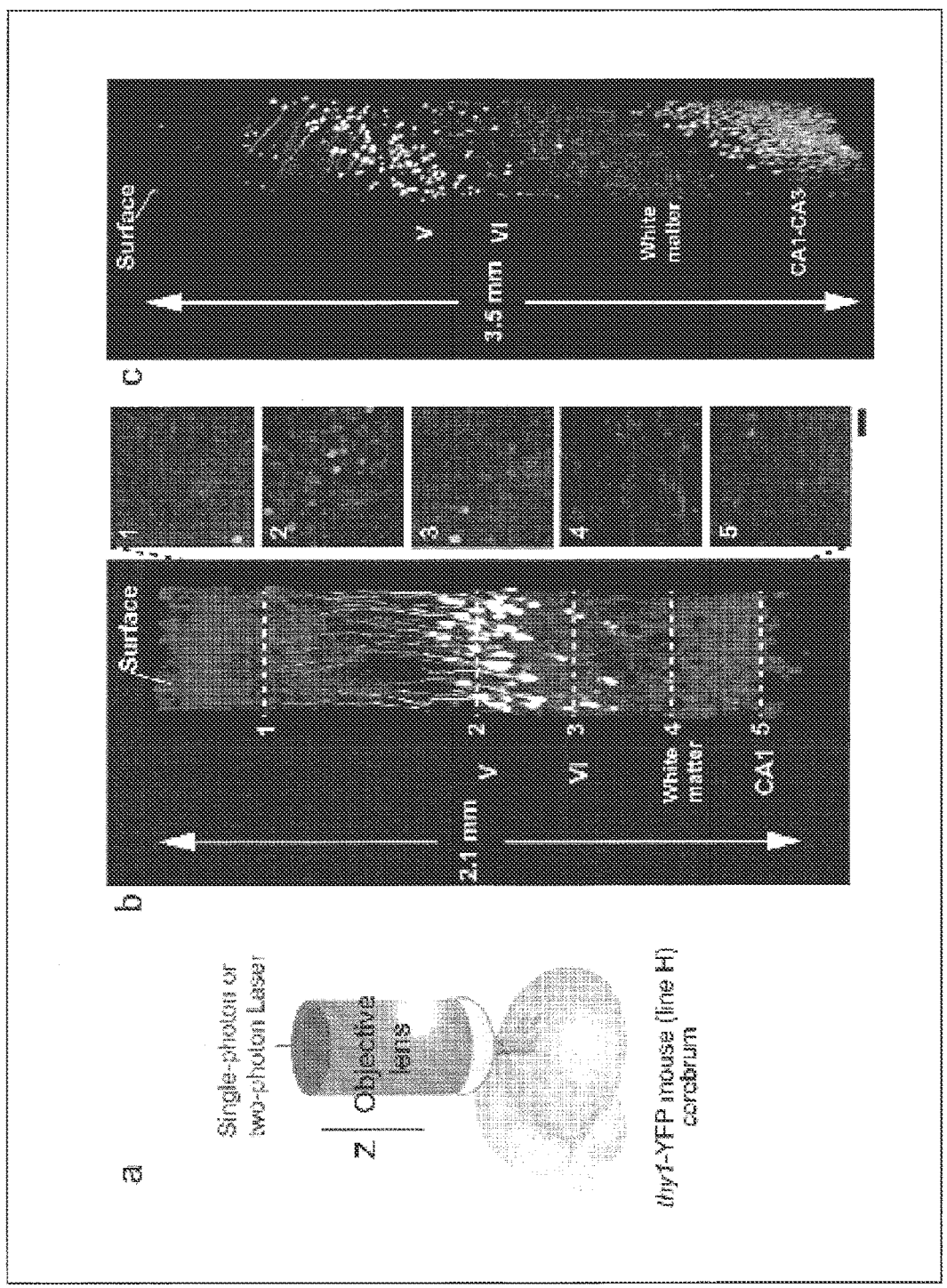
FIG. 2 is a view showing the result of another example according to the present invention.

After the staining, treatments were carried out in the same manner as in Example 1. Specifically, the cerebrum was rinsed with the antibody treatment solution and was then refixed, after which the cerebrum was treated in the solution A at room temperature for two days. Then, the cerebrum thus treated was mounted with use of 0.35 (w/v) % agarose. Subsequently, the cerebrum (7 µm-thick optical section) was observed from above the surface thereof through a laser scanning-type confocal upright microscope FV1000 (Olympus) equipped with a 20-power water immersion objective lens (Olympus; W.D.: 2 mm, NA: 0.95) ("a" in FIG. 2). Note that the observation was performed in the solution A. As a result of the observation, GFAP signals were detected in a range from the surface of the cerebrum to a depth of 2.1 mm (In FIG. 2, a side view in "b"). In FIG. 2, panels 1 to 5 in "b" are cross-sectional views taken at the depths corresponding to dotted lines drawn in the side view in "b".

Furthermore, the above cerebrums (7 µm-thick optical sections) were observed through a multi-photon laser scanning-type upright microscope FV1000 (Olympus) equipped with a 25-power water immersion objective lens (Olympus; W.D.: 4 mm, NA: 1.0) and two-photon laser ("c" in FIG. 2). A wavelength of the two-photon laser used in this observation was 920 nm, and the observation was performed in the solution A. This allowed simultaneous excitation of both the YFP and the Cy3 dye and simultaneous detection of separate signals derived from two dyes. As a result of the observation, GFAP signals were detected in a range from the surface of the cerebrum to a depth of 3.5 mm corresponding to hippocampus CA1-CA3 (In FIG. 2, a side view in "c").

Example 3: Staining Properties of Anti-Neurofilament Monoclonal Antibody with Respect to Mouse Hippocampus In the same manner as in Example 1, at the stage of sample preparation performed before the staining, an entire hippocampus of a 9 week-old C57BL6/J mouse (purchased from Japan SLC, Inc.) was subjected to immersion in the solution A and then subjected to immersion treatment in a 1×PBS. Thereafter, the hippocampus was each stained with an antibody composition which was prepared by diluting an Alexa Fluor 488 dye-labeled anti-Neurofilament mouse monoclonal antibody (Millipore) with 1 ml of antibody treatment solution (identical to the one used in Example 1). As for the Alexa Fluor 488 dye-labeled anti-Neurofilament mouse monoclonal antibody (Millipore), its antigen is a Neurofilament that serves as a marker of a neuron. As in Example 1, the antibody composition was composed of an antibody solution containing the antibody and the antibody treatment solution both of which were mixed in a volume ratio of 1:300, and an antibody concentration thereof was 10 µg/mL. The staining was carried out in such a manner that the antibody composition and the mouse hippocampus prepared by the above-described treatment were shaken at 4° C. for 3.5 days while coexisting with each other.

Figure 3:
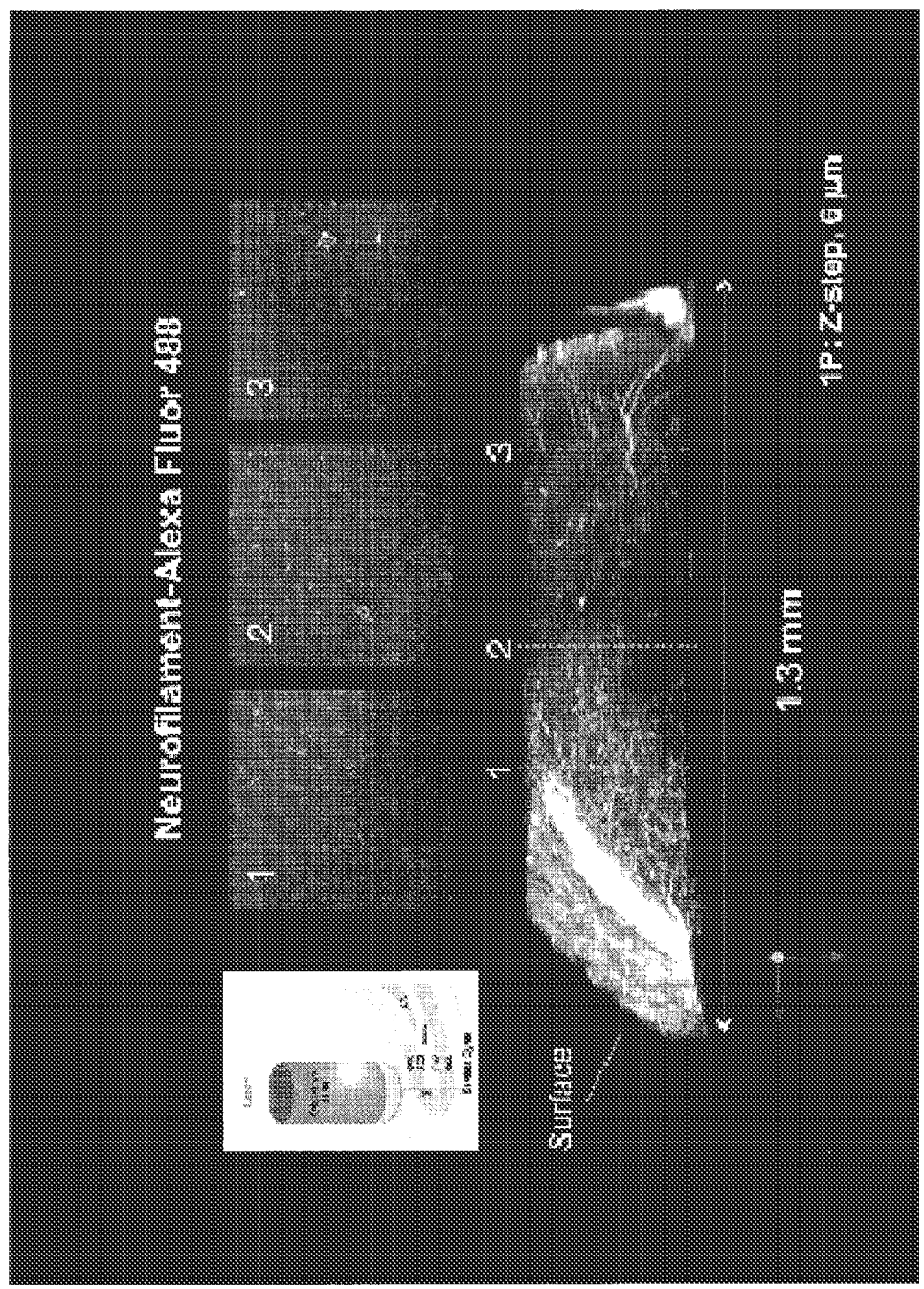
FIG. 3 is a view showing the result of further another example according to the present invention.

After the staining, treatments were carried out in the same manner as in Example 1. Specifically, the hippocampus was rinsed with the antibody treatment solution and then refixed, after which the hippocampus was mounted with use of 0.35 (w/v) % agarose. Subsequently, the hippocampus (6 µm-thick optical section) was observed from above the surface thereof through a laser scanning-type confocal upright microscope FV1000 (Olympus) equipped with a 20-power water immersion objective lens (Olympus; W.D.: 2 mm, NA: 0.95) (FIG. 3). Note that the observation was performed in the solution A (see Example 1). As a result of the observation, fibrous signals of Neurofilament, which is mainly composed of dendrites and axons, were detected in a range from the surface of the hippocampus to a depth of 1.3 mm (running through an almost entire thickness of the hippocampus) (a side view in FIG. 3). In FIG. 3, three panels 1 to 3 in FIG. 3 are cross-sectional views taken at the depths corresponding to dotted lines drawn in the side view of FIG. 3.

Example 4: Immunostaining of Neural Stem Cell Markers with Respect to Neural Stem Cells, Neurosphere, Derived from Adult Rat Hippocampus After prepared from an 8 to 10 week-old rat, hippocampus-derived neural stem cells maintaining purification and passage were dispersed in a culture medium and then subjected to suspension culturing for 12 days on the basis of the descriptions of reference (Doetsch et al. Cell, 97: 703-716, 1999) to form neurospheres. The neurosphere is a cluster of tightly aggregating cells. Hence, there is a difficulty in permeating antibodies into the neurosphere. The neurosphere, despite its relatively small size, is subjected to immunostaining with difficulty. This spherical cell clusters (neurospheres) were fixed in a 4% PFA-PBS, after which the neurospheres were replaced by a 20 (w/v) %, sucrose-PBS at 4° C. for two days and were then subjected to cryoprotection. Thereafter, the neurospheres were embedded into an OCT compound and thawed. Subsequently, the neurospheres were cleaned with 1×PBS and refixed in a 4% (w/v) PFA-PBS. Then, the neurospheres were immersed in the solution A, which is identical to the one used in Example 1, shaken at room temperature for three days, and then subjected to immersion treatment in a 1×PBS for one hour.

Subsequently, the neurospheres were stained with two kinds of antibody compositions containing primary antibodies. The antibody compositions used in the staining were as follows:

1) An antibody composition prepared by diluting an anti-Nestin mouse monoclonal antibody (BD Bioscience) with 1 ml of antibody treatment solution (identical to the one used in Example 1). The antibody composition was composed of an antibody solution containing the antibody and the antibody treatment solution both of which were mixed in a volume ratio of 1:300, and an antibody concentration thereof was 6 µg/mL. This antibody recognizes a neural stem cell.

2) An antibody composition prepared by diluting an anti-Doublecortin rabbit polyclonal antibody (abcam) with 1 ml of antibody treatment solution (identical to the one used in Example 1). The antibody composition was composed of an antibody solution containing the antibody and the antibody treatment solution both of which were mixed in a volume ratio of 1:200, and an antibody concentration thereof was 7 µg/mL. This antibody recognizes an immature neuron.

The staining was carried out in such a manner that each of these antibody compositions and the neurosphere prepared by the above-described treatment were shaken at 4° C. for two days while coexisting with each other. Subsequently, the primary antibodies were each rinsed with the above antibody treatment solution (12 ml for each 0.3 g of tissue (neurosphere)) by one-hour shaking at room temperature.

After subjected to the rinsing, the neurospheres were each stained with (i) an antibody composition prepared by diluting an Alexa Fluor 488-labeled anti-mouse IgG-antibody, as a secondary antibody, with 1 ml of the above antibody treatment solution and (ii) an antibody composition prepared by diluting an Alexa Fluor 633-labeled anti-rabbit IgG-antibody, as a secondary antibody, with 1 ml of the above antibody treatment solution. Note that these antibody compositions were each composed of an antibody solution containing the antibody and the antibody treatment solution both of which were mixed in a volume ratio of 1:500, and antibody concentrations thereof were each 4 µg/mL. The staining was carried out in such a manner that each of these antibody compositions and the neurosphere were then shaken at 4° C. for 24 hours while coexisting with each other. Subsequently, the secondary antibodies were each rinsed with the above antibody treatment solution (12 ml for each 0.3 g of tissue (neurosphere)) by one-hour shaking at room temperature.

Subsequently, the neurosphere was stained with an antibody composition prepared by diluting an anti-GFAP-Cy3 mouse monoclonal antibody (Sigma), which recognized an astrocyte, with 1 ml of antibody treatment solution (identical to the one used in Example 1). This antibody composition was composed of an antibody solution containing the antibody and the antibody treatment solution both of which were mixed in a volume ratio of 1:300, and an antibody concentration thereof was 7 µg/mL. The staining was carried out in such a manner that the neurosphere was shaken at 4° C. for 24 hours while coexisting with the antibody composition, thereby being reacted with the antibody composition for staining. Thereafter, the neurosphere was rinsed and refixed, after which the neurosphere was immersed in the solution A (see Example 1) and was then shaken for incubation at room temperature for two days. Finally, the neurosphere thus treated was mounted with use of 0.35 (w/v) % agarose.

The neurosphere thus mounted was observed (with respect to 6 µm-thick optical section thereof) in the solution A through a laser scanning-type confocal upright microscope FV1000 (Olympus) equipped with a 20-power water immersion objective lens (Olympus; W.D.: 2 mm, NA: 0.95).

Figure 4:
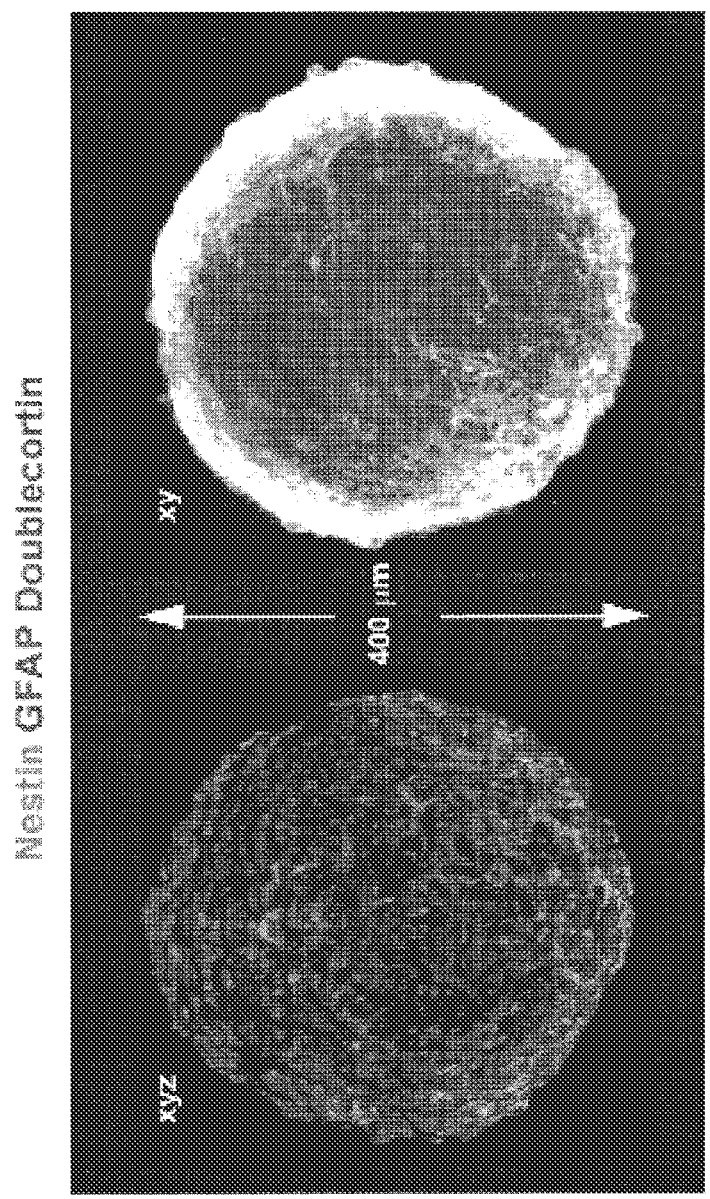
FIG. 4 is a view showing the result of still further another example according to the present invention.

It was possible to comprehensively observe the entire neurosphere (approximately 400 µm in diameter) covering all the ranges from its surface to internal portions. It was possible to detect what kind of cells are present in the neurosphere and the localization of the cell, and it was observed that neural stem cells were unevenly distributed over the surface of the neurosphere, whereas immature neurons differentiated from stem cells were present within the neurosphere. In FIG. 4, a view on the left-hand side shows a three-dimensional fluoroscopic image prepared by using Volocity, and a view on the right-hand side shows a cross-sectional view taken at a position corresponding to a maximum diameter of the neurosphere.

Example 5: Immunostaining of a Newborn Neuron in a Mature Mouse Brain

A cerebrum of a 8 week-old Nestin promoter-driven GFP transgenic mouse (Nestin-GFP mouse, Reference: Yamamoto et al., Neuroreport, 11: 1991-1996, 2000), in which neural stem cells showed green fluorescence, was separated into left and right hemispheres along a midline. The cerebral hemisphere was immersed in the solution A of the same composition as in Example 1 and was then shaken at room temperature for about 3 weeks, after which the cerebral hemisphere was subjected to immersion treatment in a 1×PBS for twelve hours.

Subsequently, the cerebral hemisphere was stained with two kinds of antibody compositions containing primary antibodies. The antibody compositions used in the staining were as follows:

1) An antibody composition prepared by diluting an anti-GFAP-Cy3 mouse monoclonal antibody (Sigma) with 1 ml of antibody treatment solution (identical to the one used in Example 1). The antibody composition was composed of an antibody solution containing the antibody and the antibody treatment solution both of which were mixed in a volume ratio of 1:400, and an antibody concentration thereof was 7 µg/mL.

2) An antibody composition prepared by diluting an anti-Doublecortin rabbit polyclonal antibody (abcam) with 1 ml of antibody treatment solution (identical to the one used in Example 1). The antibody composition was composed of an antibody solution containing the antibody and the antibody treatment solution both of which were mixed in a volume ratio of 1:200, and an antibody concentration thereof was 10 µg/mL. This antibody recognizes an immature neuron.

The staining was carried out in such a manner that each of these antibody compositions and the cerebral hemisphere prepared by the above-described treatment were shaken at ° C. for four days while coexisting with each other. Subsequently, the primary antibodies were each rinsed with the above antibody treatment solution (12 ml for each 0.3 g of tissue (cerebral hemisphere)) by one-hour shaking at room temperature.

After the rinsing of the primary antibodies, the cerebral hemisphere was stained with (i) an antibody composition prepared by diluting an Alexa Fluor 488-labeled anti-mouse IgG-antibody, as a secondary antibody, with 1 ml of antibody treatment solution (identical to the one used in Example 1) and (ii) an antibody composition prepared by diluting an Alexa Fluor 633-labeled anti-rabbit IgG-antibody, as a secondary antibody, with 1 ml of antibody treatment solution (identical to the one used in Example 1). Note that these antibody compositions were each composed of an antibody solution containing the antibody and the antibody treatment solution both of which were mixed in a volume ratio of 1:500, and antibody concentrations thereof were each 4 µg/mL. The staining was carried out in such a manner that each of the above antibody compositions and the cerebral hemisphere were shaken at 4° C. for two days while coexisting with each other. Subsequently, the secondary antibodies were each rinsed with the above antibody treatment solution (12 ml for each 0.3 g of tissue (cerebral hemisphere)) by four-day shaking at room temperature.

Subsequently, the cerebral hemisphere was refixed, after which the cerebral hemisphere was immersed in the solution A (see Example 1) and was then shaken for incubation at room temperature for two days. Finally, the cerebral hemisphere thus treated was mounted with its cut section facing upward, with use of 0.35 (w/v) % agarose and was then immersed in the solution A.

The cerebral hemisphere thus mounted was observed in the solution A through a laser scanning-type confocal upright microscope FV1000 (Olympus) equipped with a 20-power water immersion objective lens (Olympus; W.D.: 2 mm, NA: 0.95). The observation was multipoint observation performed on 50 visual fields, wherein an observation depth was 1.6 mm, and an optical section was 7 µm in thickness.

For mature rodents, it is known that nerves are newly born (neurogenesis) from neural stem cells that present primarily in two regions, i.e. hippocampus and subventricular zone. Neural stem cells grown in a subventricular zone near a lateral ventricle moves a long distance toward an olfactory bulb while being sequentially differentiated into blast or immature neurons, and are eventually incorporated into a neural tissue of the olfactory bulb. Such a continuous movement is known as rostral migratory stream (RMS). The present Example demonstrates that a cell group constituting the RMS was identified by immunostaining.

Figure 5:
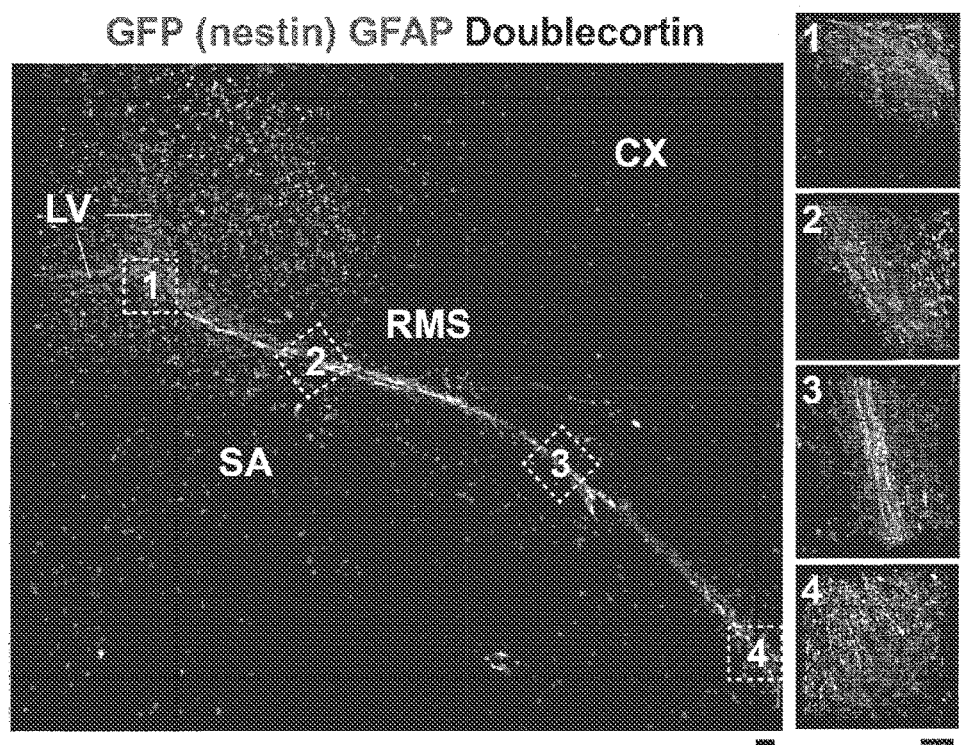
FIG. 5 is a view showing the result of yet another example according to the present invention.

More specifically, as shown in FIG. 5, it was demonstrated that a continuous cell stream of neural stem cells was formed by being differentiated into immature neurons while moving forward from the lateral ventricle as a starting point. Furthermore, it was demonstrated that this stream was surrounded by a tube or tunnel made up of assembled astrocytes and moved through the tube or tunnel. In FIG. 5, respective regions surrounded by squares numbered 1 to 4 are shown together with views of their corresponding three-dimensional fluoroscopic images obtained by enlarging the respective regions. The staining as described above has become possible and is expected to serve as an important means in a comprehensive study on the differentiation of neural stem cells in a deep and wide area.

Example 6: Immunostaining of Nerve Ending of Mouse Hippocampus

A hippocampus separated from a cerebrum of a 7 week-old ICR mouse (purchased from Japan SLC, Inc.) was fixed in a 4% PFA-PBS, after which the hippocampus was immersed in the solution A which is composed as in Example 1, and shaken at room temperature for 10 days. Thereafter, the hippocampus was subjected to immersion treatment in a 1×PBS for twelve hours.

Subsequently, the hippocampus thus treated was stained in its entirety with an antibody composition prepared by diluting an Oyster 650-labeled anti-synaptophysin mouse monoclonal antibody (Synaptic Systems), which recognizes a protein that presents in a vesicle of a presynaptic terminal, with 1 ml of antibody treatment solution (identical to the one used in Example 1). The antibody composition was composed of an antibody solution containing the antibody and the antibody treatment solution both of which were mixed in a volume ratio of 1:200, and an antibody concentration thereof was 10 µg/mL. The staining was carried out in such a manner that the antibody composition and the hippocampus were shaken at room temperature for three days while coexisting with each other.

After the staining, the hippocampus was rinsed with the antibody treatment solution and was then refixed, after which the hippocampus was immersed in the solution A (see Example 1) and then shaken for incubation at room temperature for two days. Finally, the hippocampus thus treated was mounted with its dentate gyrus facing upward with use of 0.35 (w/v) % agarose and was then immersed in the solution A.

Subsequently, the hippocampus thus mounted was observed in the solution A through a laser scanning-type confocal upright microscope FV1000 (Olympus) equipped with a 20-power water immersion objective lens (Olympus; W.D.: 2 mm, NA: 0.95). The observation was performed such that an observation depth was 1.4 mm, and an optical section was 5 µm in thickness (also see "a" in FIG. 6).

Figure 6:
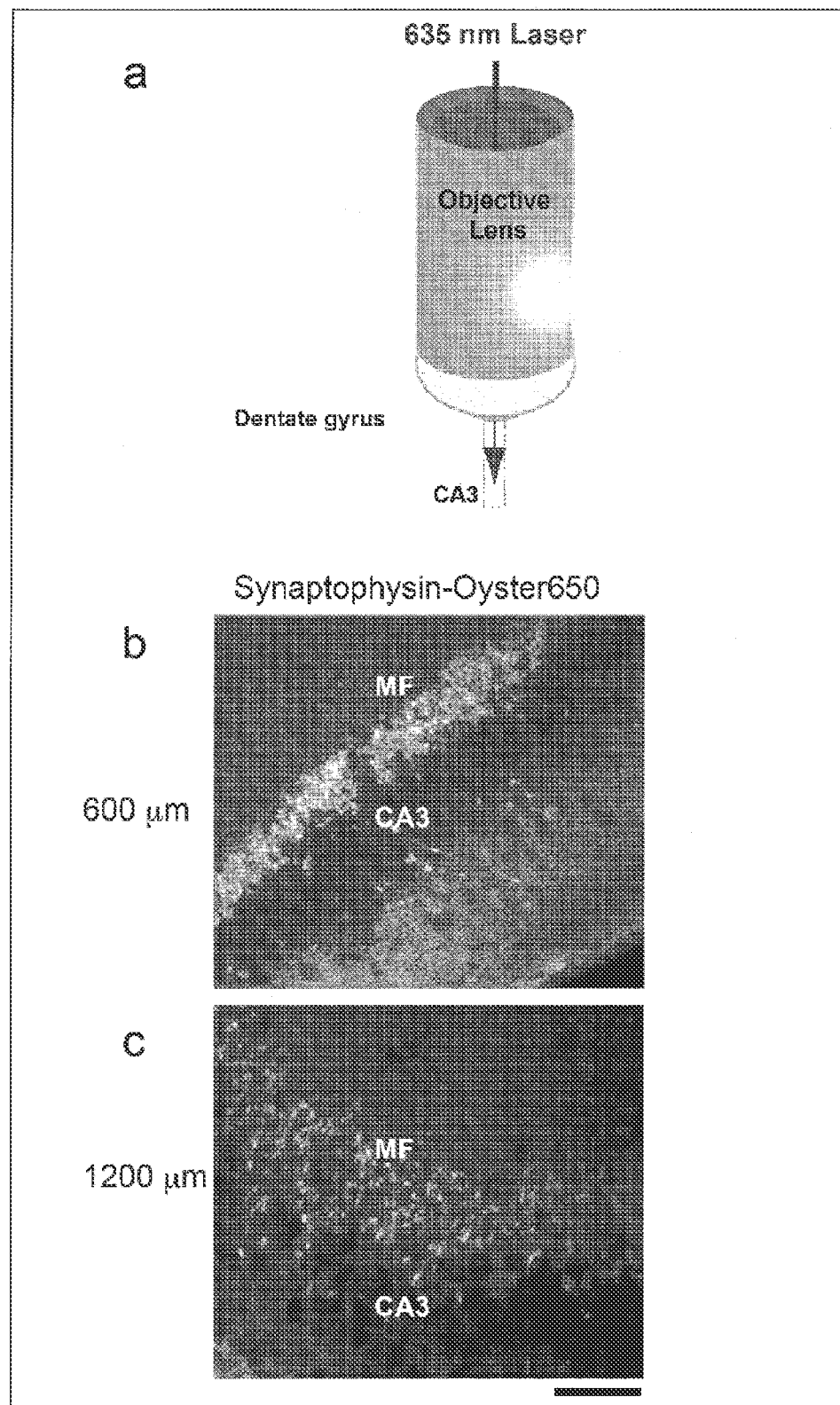
FIG. 6 is a view showing the result of still yet another example according to the present invention.

Axons of granule cells originating from the dentate gyrus allow characteristic mossy fibers (mossy fiber, MF) to be projected onto the CA3 region, and a giant synapse is formed between the axons and pyramidal cells of CA3. In FIG. 6, white particle-like signals are observed in the cross-sectional views taken at the depths in "b" and "c". These signals are signals of synaptophysin that present in a vesicle of a nerve ending. It is therefore considered that the giant synapse is formed at a site where the signals of synaptophysin were detected.

As shown in FIG. 6, it was confirmed that the Oyster 650-labeled antibody permeated the tissue at both of the depths of 600 µm and 1300 µm. The staining as described above has become possible and therefore makes it possible to avoid a complicated process of observing a great number of slices subjected to immunostaining, and to observe, at once, whether or not synapses are formed in projection destinations of nerve fibers in various regions in a brain by using, for example, a whole tissue. That is, the staining as described above can be considered to play an important role in making a study on neural circuits with efficiency.

Example 7: Immunostaining of β-Amyloid in Hippocampus of an Amyloid Precursor Protein-Presenilin 1 Overexpressing Mouse From a cerebrum of a 23 month-old amyloid precursor protein-presenilin 1 overexpressing mouse (Saito et al. Nature Neuroscience 14(8):1023-1032, 2011), a brain sample having thalamus detached therefrom and having hippocampus exposed to view was prepared. The brain sample was fixed in a 4% PFA-PBS. Subsequently, the brain sample was immersed in the solution A of the same composition as in Example 1 and was then shaken at room temperature for 20 days, after which the brain sample was subjected to immersion treatment in a 1×PBS for 24 hours.

Subsequently, the hippocampus thus treated was stained in its entirety with (i) an antibody composition prepared by diluting an AlexaFluor 488-labeled anti-β-amyloid mouse monoclonal antibody (Cocvance, clone 6E10) with 1 ml of antibody treatment solution (identical to the one used in Example 1) and (ii) an antibody composition prepared by diluting an anti-GFAP-Cy3 mouse monoclonal antibody (Sigma) with 1 ml of antibody treatment solution (identical to the one used in Example 1). The staining was carried out in such a manner that each of these antibody compositions and the hippocampus were shaken at room temperature for four days while coexisting with each other. The antibody composition containing the Alexa Fluor 488-labeled anti-β-amyloid mouse monoclonal antibody was composed of an antibody solution containing the antibody and the antibody treatment solution both of which were mixed in a volume ratio of 1:300, and an antibody concentration thereof was 10 μg/mL. The antibody composition containing the anti-GFAP-Cy3 mouse monoclonal antibody was composed of an antibody solution containing the antibody and the antibody treatment solution both of which were mixed in a volume ratio of 1:400, and an antibody concentration thereof was 7 μg/mL.

After the staining, the hippocampus was rinsed with the antibody treatment solution and was then refixed, after which the hippocampus was immersed in the solution A and then shaken for incubation at room temperature for two days. Finally, the hippocampus thus treated was mounted with its dentate gyrus facing upward with use of 0.35 (w/v) % agarose and was then immersed in the solution A.

Figure 7:
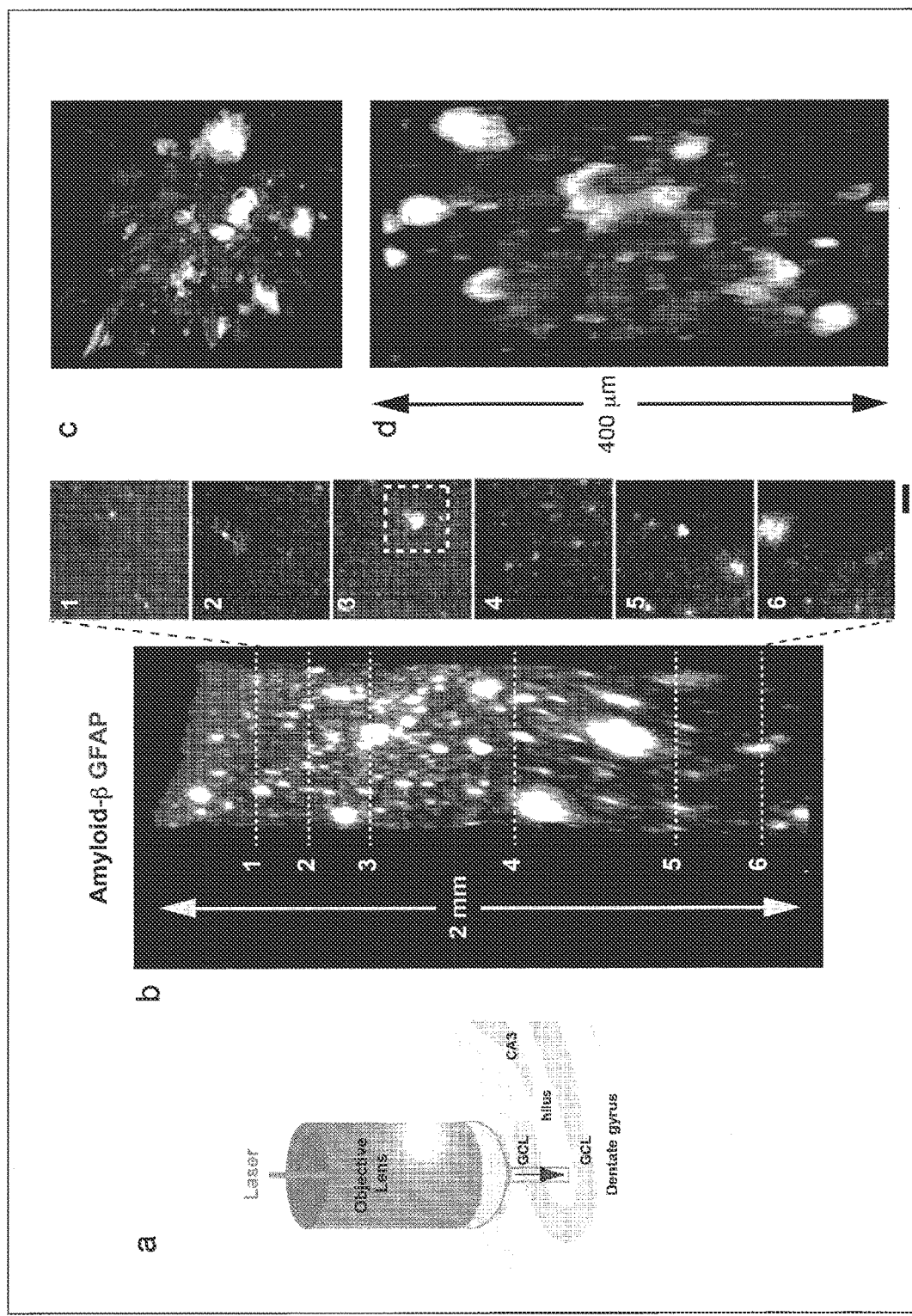
FIG. 7 is a view showing the result of further another example according to the present invention.

Subsequently, the hippocampus thus mounted was observed in the solution A through a laser scanning-type confocal upright microscope FV1000 (Olympus) equipped with a 20-power water immersion objective lens (Olympus; W.D.: 2 mm, NA: 0.95). The observation was performed such that an observation depth was 2 mm, and an optical section was 7 μm in thickness (also see FIG. 7). In FIG. 7, panels 1 to 6 in "b" are cross-sectional views taken at the depths corresponding to dotted lines 1 to 6 drawn in "b" of FIG. 7.

Accumulation of β-amyloid is believed to be an important factor contributing to the pathogenesis of severe Alzheimer's disease in humans. From the view showing an immunostained image of the mouse, it is observed that a myriad of amyloid plaques consisting of large and small β-amyloids exist in all of the regions covering from the surface of the hippocampus to the deep portion. Such an aspect is significantly different from that of a normal tissue. Specifically, a pathological aspect known as gliosis is found in which astrocytes, GFAP-positive cells, are densely present around a huge plaque. In FIG. 7, "c" is a top view showing a three-dimensional fluoroscopic image of an area surrounded by a dotted square in panel 3 in "b". In FIG. 7, "d" is a side view showing a three-dimensional fluoroscopic image of the same area.

As demonstrated in the present Example, it has become possible to subject a diseased tissue to immunostaining in a collective manner. This provides an extremely effective means for "successful pathology search without unexpected defeat" in order to perform more detailed pathological search than ever.

INDUSTRIAL APPLICABILITY

The present invention is applicable to all industries using antigen-antibody reactions, including antibody-containing reagents. Example applications of the present invention include reagents using antigen-antibody reactions, diagnostic applications, and pharmaceutical development.

The invention claimed is:
1. An immunostaining method comprising:
a step of preparing an antibody composition, the antibody composition comprising:
at least one compound selected from the group consisting of urea and urea derivatives, wherein the urea derivatives are encompassed within the following formula I:

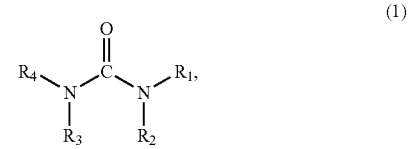

wherein in the Formula (1), each of R1, R2, R3 and R4 is independently a hydrogen atom, a halogen atom, or a hydrocarbon group, where the one in which all of R1, R2, R3 and R4 are hydrogen atoms is excluded, and in a case where the hydrocarbon group has a plurality of carbon atoms, part of the carbon atoms may be replaced by a hetero atom such as a nitrogen atom, an oxygen atom, or a sulfur atom; and
an antibody for immunostaining,
the compound being contained in the antibody composition at a concentration of not less than 0.1 M and less than 1 M,
a step of bringing the antibody composition and a biological material into contact with each other to allow an antigen-antibody reaction to occur between the antibody and the biological material,
the antibody composition being a solution,
wherein the antibody stains the biological material.
2. The method as set forth in claim 1, wherein the compound is contained in the antibody composition at a concentration of not less than 0.2 M and not more than 0.5 M.
3. The method as set forth in claim 1, wherein the antibody composition contains a surfactant.
4. The method as set forth in claim 3, wherein the surfactant is a nonionic surfactant.
5. The method as set forth in claim 4, wherein the nonionic surfactant is at least one selected from the group consisting of TRITON X (Registered Trademark), TWEEN (Registered Trademark), and NP-40 (product name).
6. The method as set forth in claim 3, wherein the surfactant is contained at a concentration of not less than 0.025 (w/v) % and not more than 0.2 (w/v) %.
7. The method as set forth in claim 1, wherein the antibody is contained at a concentration of not less than 0.05 μg/mL and not more than 100 μg/mL.
8. The method as set forth in claim 1, wherein the antibody composition comprises urea.

* * * * *